US00PP30576P2

(12) United States Plant Patent
Nicolaï

(10) Patent No.: US PP30,576 P2
(45) Date of Patent: Jun. 18, 2019

(54) APPLE TREE NAMED 'ZOUK G1'

(50) Latin Name: *Malus domestica Mill.*
Varietal Denomination: ZOUK G1

(71) Applicant: Zouk B.V.B.A., Sint-Truiden (BE)

(72) Inventor: Johan Nicolaï, Sint-Truiden (BE)

(73) Assignee: Zouk B.V.B.A, Sint-Truiden (BE)

( * ) Notice: Subject to any disclaimer, the term of this patent is extended or adjusted under 35 U.S.C. 154(b) by 0 days.

(21) Appl. No.: 15/732,502

(22) Filed: Nov. 20, 2017

(51) Int. Cl.
*A01H 5/08* (2018.01)
*A01H 6/74* (2018.01)

(52) U.S. Cl.
USPC ..... Plt./161
CPC ..... *A01H 6/7418* (2018.05)

(58) Field of Classification Search
USPC ..... Plt./162, 161
CPC ..... A01H 5/0875; A01H 5/08; A01H 6/7418; A01H 6/749; A01H 5/02; A01H 5/0222
See application file for complete search history.

(56) References Cited

U.S. PATENT DOCUMENTS

| | | | | | |
|---|---|---|---|---|---|
| PP4,121 | P | | 10/1977 | ten Hove | |
| PP6,450 | P | * | 12/1988 | Visser | Plt./161 |
| PP6,955 | P | * | 8/1989 | Kiddle | Plt./162 |
| PP16,559 | P3 | | 5/2006 | Nicolai | |
| PP17,201 | P3 | | 11/2006 | Nicolai | |
| PP25,671 | P3 | * | 7/2015 | Kellerhals | A01H 5/00 Plt./161 |
| 2004/0025211 | P1 | * | 2/2004 | Zulch | A01H 5/0875 Plt./162 |

OTHER PUBLICATIONS

Guerra. EFM Jun. 2017 Strains improve standard varieties translated and edited by Julia Strobl, retrieved on Oct. 22, 2018, retrieved from the Internet at http://kp.eufrin.eu/fileadmin/user_upload/documents/804-14df1cca1323ccb72d8b027c37356dfd.pdf, pp. 14-17. (Year: 2017).*

Horticulture Week Applie varieties found by chance unveiled at show 2015, retrieved on Oct. 22, 2018, retrieved from the Internet at https://www.hortweek.com/apple-varieties-found-chance-unveiled-show/fresh-produce/article/1370357, 2 pp. (Year: 2015).*

U.S. Appl. No. 15/732,499, "Apple Tree Named 'Zouk 31'," filed Nov. 20, 2017, for inventor Johan Nicolai and for applicant Zouk B.V.B.A.

U.S. Appl. No. 15/732,496, "Apple Tree Named 'Zouk 16'," filed Nov. 20, 2017, for inventor Johan Nicolai and for applicant Zouk B.V.B.A.

U.S. Appl. No. 15/732,497, "Apple Tree Named 'Zouk 32'," filed Nov. 20, 2017, for inventor Johan Nicolai and for applicant Zouk B.V.B.A.

Fresh Plaza (2016). "Johan Nicolai presents new early Gala variety," retrieved on Oct. 16, 2018 from the Internet at http://www.freshplaza.com/article/2153468/johan-nicolai-presents-new-early-gala-variety/, 2 pp.

* cited by examiner

*Primary Examiner* — June Hwu
(74) *Attorney, Agent, or Firm* — Morrison & Foerster LLP

(57) ABSTRACT

A new and distinctive variety of a *Malus domestica* Mill. apple tree, named 'ZOUK G1' that is distinguished by its early ripening and good coloring characteristics, and by fruit that is striped and dark red in color with a sweet flavor and crisp texture, is disclosed.

6 Drawing Sheets

LATIN NAME

Botanical classification: *Malus domestica* Mill.

VARIETAL DENOMINATION

The varietal denomination of the claimed apple tree variety is 'ZOUK G1'.

BACKGROUND OF THE INVENTION

Apples are an economically important crop. Accordingly, there exists a need to develop new varieties of apple tree with improved characteristics, such as fruit appearance and quality.

BRIEF SUMMARY OF THE INVENTION

In order to meet these needs, the present invention is directed to an improved variety of apple tree. In particular, the invention relates to a new and distinct variety of apple tree (*Malus domestica* Mill.), which has been denominated as 'ZOUK G1'.

Apple tree variety 'ZOUK G1' is a mutant tree that was discovered as a branch mutation in a commercial crop of apple tree variety 'Royal Beaut' (U.S. Plant Patent Application Publication No. 2004/0025211 P1) conducted in Sint-Truiden, Belgium in 2012. The mutant was first asexually propagated by T-budding and bench grafting onto 'M9 T337' rootstock (also known as 'M9' or 'M9 NAKBT337'; unpatented), 'MM106' rootstock (also known as 'Malling-Merton 106'; unpatented), and 'MM111' rootstock (also known as 'Malling-Merton 111'; unpatented) in 2013 and subsequently planted in a nursery bed for tree production.

The new apple tree variety 'ZOUK G1' was selected for its early ripening characteristics and fruit with good coloring properties. Fruit of 'ZOUK G1' is striped with a dark red color and has a sweet flavor and crisp texture.

Asexual reproduction of the 'ZOUK G1' apple tree variety by T-budding and bench grafting onto 'M9 T337', 'MM106' and 'MM111' rootstocks in Sint-Truiden, Belgium shows that the foregoing and all other characteristics and distinctions are true to type and are established and transmitted through succeeding asexual propagations.

BRIEF DESCRIPTION OF THE DRAWINGS

The 'ZOUK G1' apple tree variety is illustrated by the accompanying photographs which show fruit of the tree, as well as the flowers. The colors shown are as true as can be reasonably obtained by conventional photographic procedures. However, the colors in the photographs may vary with lighting conditions and, therefore, color characteristics of this new variety should be determined with reference to the observations described herein, rather than from the photographs alone. The photographs are from trees that are four years old.

As shown in FIG. 4, 'ZOUK G1' is in full bloom whereas 'Royal Beaut' is at pink stage.

FIG. 5A shows whole fruit of apple tree variety 'ZOUK G1' (two fruit on left) and whole fruit of apple tree variety 'Royal Beaut' (two fruit on right) approximately 4 weeks before harvest. FIG. 5B shows whole fruit of apple tree variety 'ZOUK G1' (two fruit on left) and whole fruit of apple tree variety 'Royal Beaut' (two fruit on right) approximately 2 weeks before harvest of 'ZOUK G2'. FIG. 5C shows whole fruit approximately 2 weeks before harvest of 'ZOUK G1'; in the bottom row, the two fruit on the left are from apple tree variety 'ZOUK G1' and the three fruit on the right are from apple tree variety 'Royal Beaut', and in the top row, the four apples on the left are from apple tree variety 'ZOUK G1', and the one apple on the right is from apple tree variety 'Royal Beaut'. FIG. 5D shows horizontal cross-sections of fruit of apple tree variety 'ZOUK G1' (on the left) and fruit of apple tree variety 'Royal Beaut' (on the right) three days before harvest of 'ZOUK G1', which have been stained with iodine.

DETAILED BOTANICAL DESCRIPTION

Figure 1:
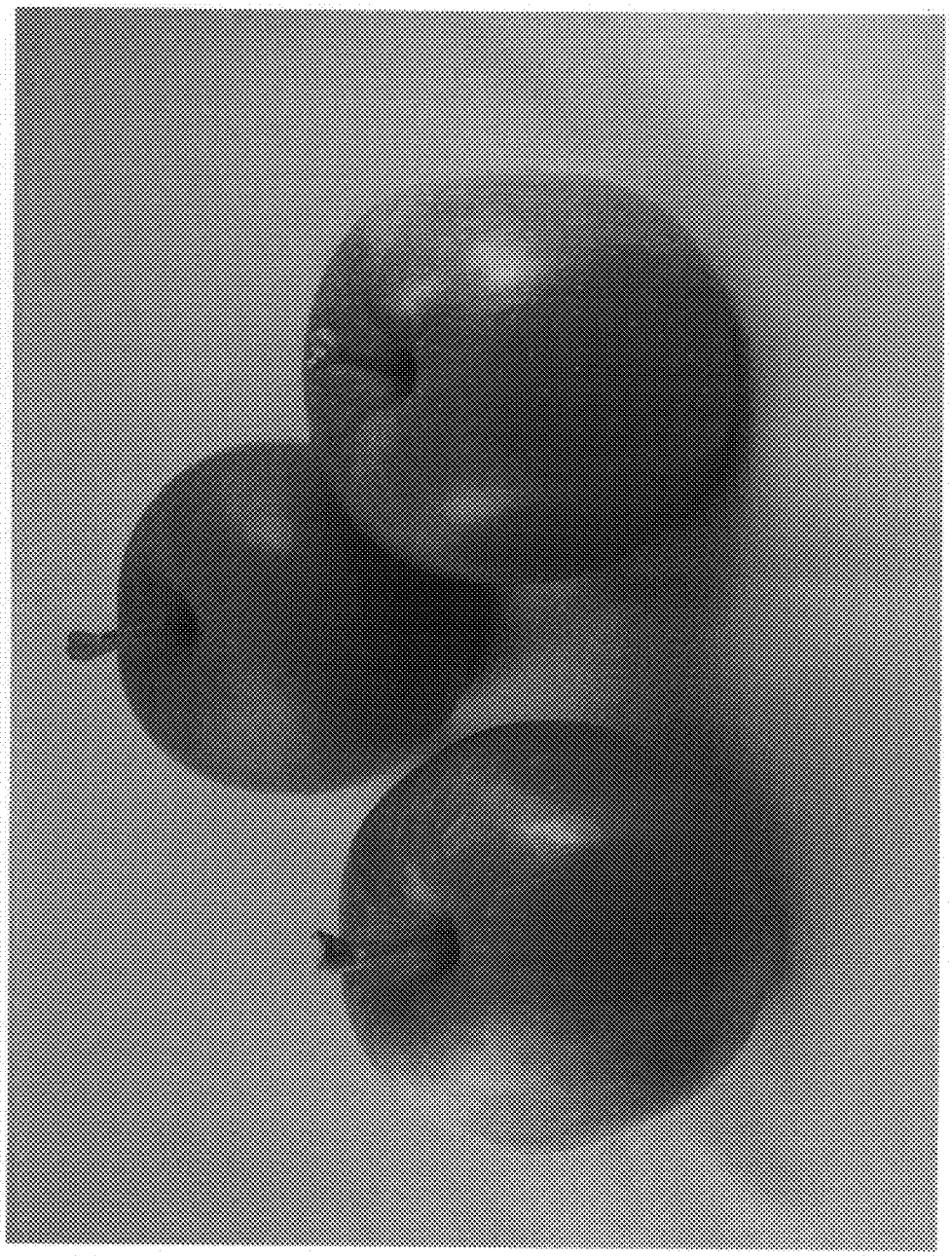
FIG. 1 illustrates fruits of apple tree variety 'ZOUK G1'.
Figure 2:
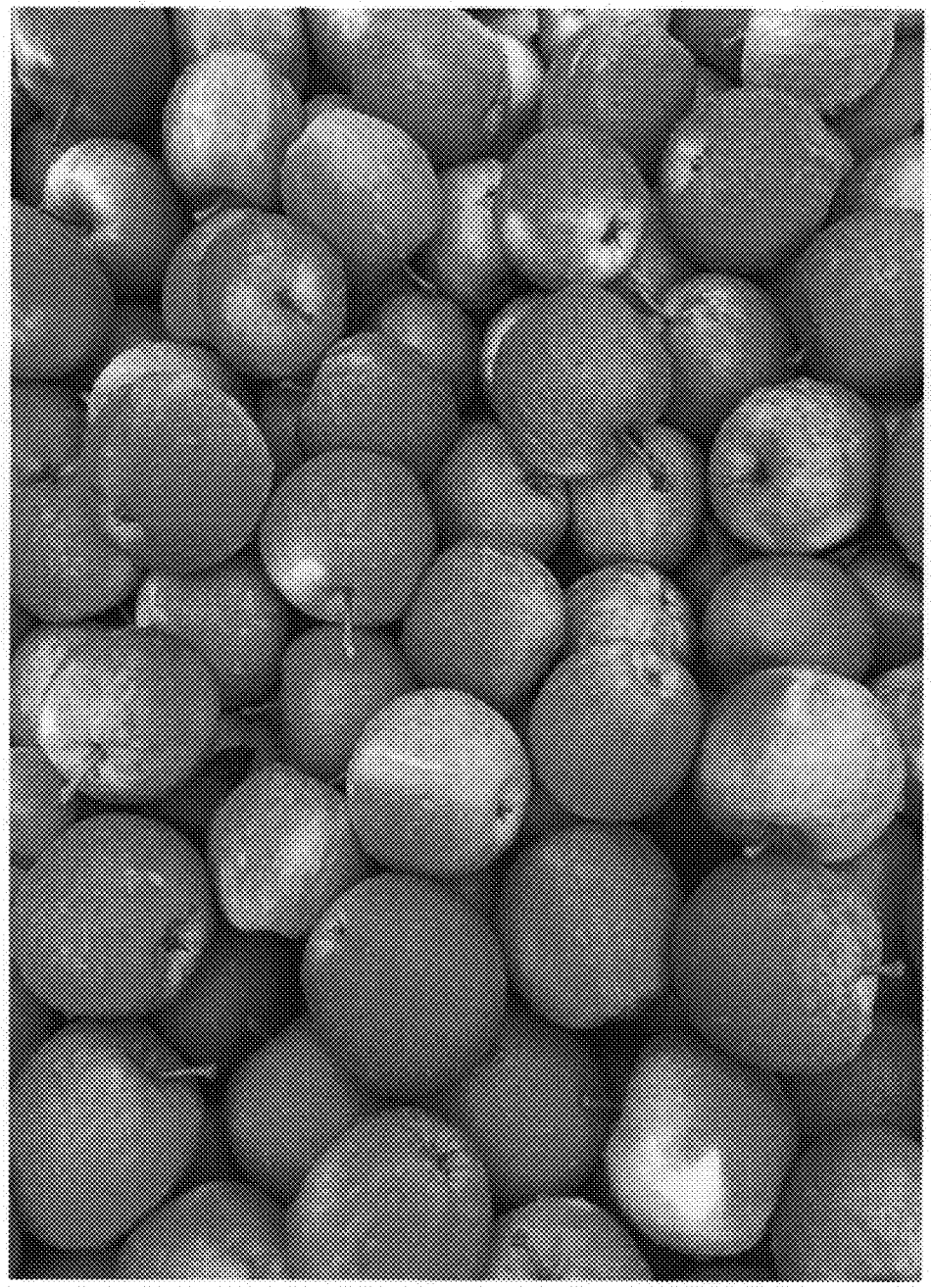
FIG. 2 illustrates fruits of apple tree variety 'ZOUK G1' at harvest.
Figure 3:
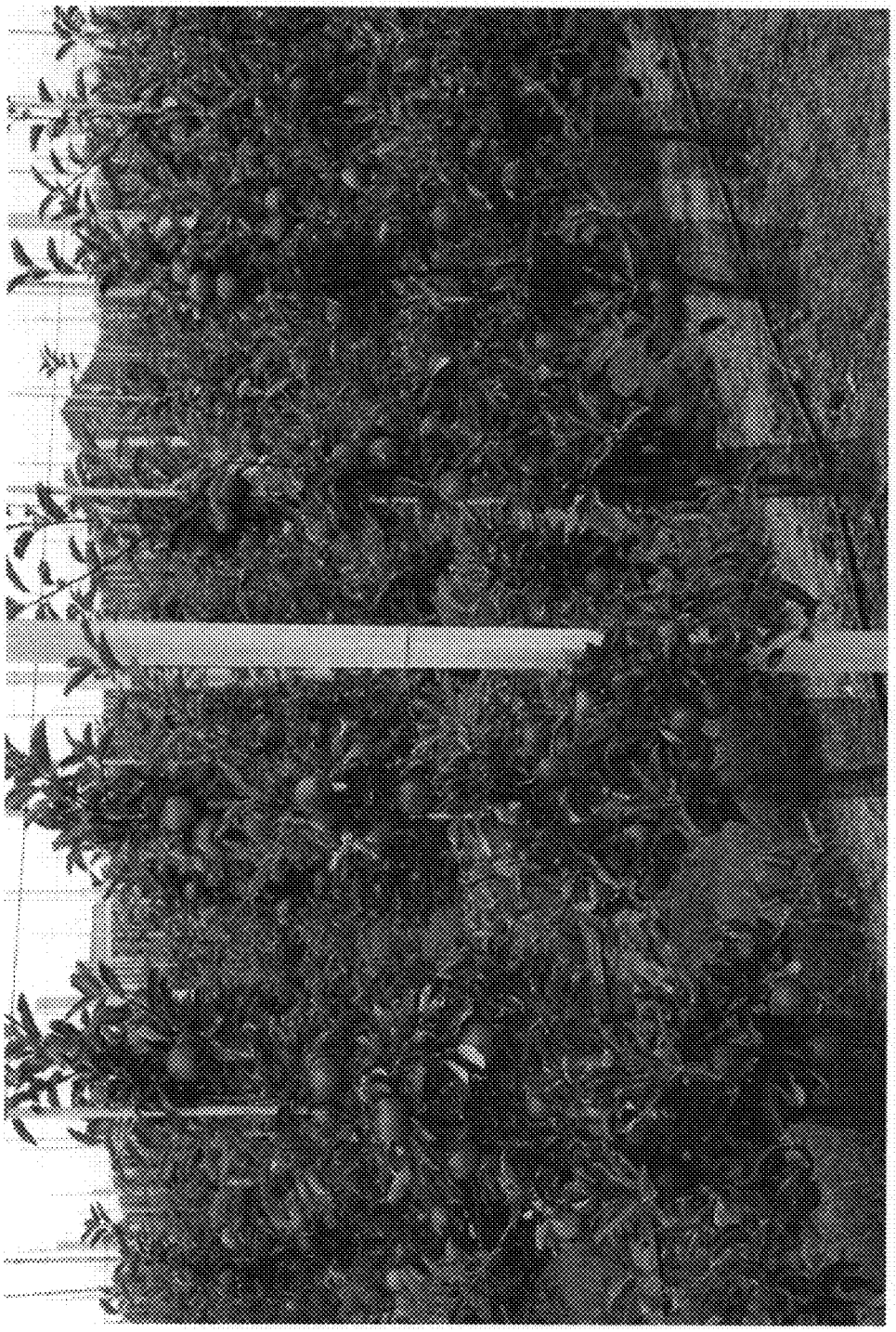
FIG. 3 illustrates a tree of apple tree variety 'ZOUK G1' with fruit on the tree.
Figure 4:
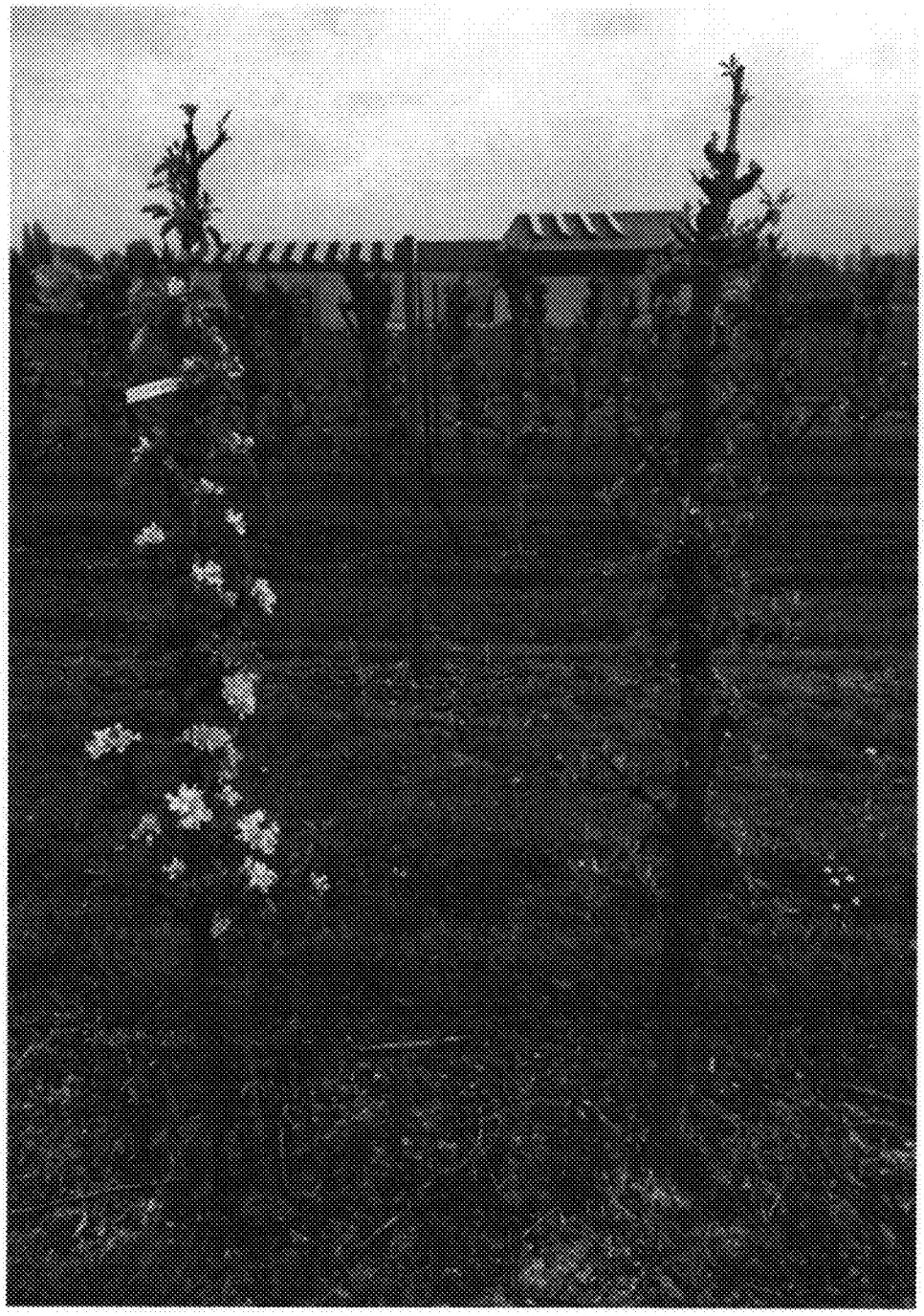
FIG. 4 illustrates the difference in blooming between apple tree varieties 'ZOUK G1' (on the left) and 'Royal Beaut' (on the right).

The following description sets forth the distinctive characteristics of 'ZOUK G1'. The following botanical description of 'ZOUK G1' is based on observations of the originally identified tree, and asexually reproduced progeny, grown on 'M9 T337' rootstock in Sint-Truiden, Belgium. Referring more specifically to the details of the new and distinct variety of apple tree, unless otherwise stated, the following has been observed on trees that were four years of age growing on 'M9 T337' rootstock in Sint-Truiden, Belgium. Numbers provided are averages of data measured from the sampling trees.

Certain characteristics, as well as the phenotype, of this variety may vary with changing environmental conditions (e.g., light, temperature, moisture, etc.), nutrient availability, or other factors. Quantified measurements are expressed as an average of measurements taken from a number of individual plants of the new variety. The measurements of any individual plant, or any group of plants, of the new variety may vary from the stated average. Color descriptions and other terminology are used in accordance with their ordinary dictionary descriptions, unless the context clearly indicates otherwise. All color references are from The R.H.S. Colour Chart of The Royal Horticultural Society of London (R.H.S.) (Sixth Edition, 2015).

Tree:

*Vigor*.—Medium (comparable to 'Royal Beaut' (U.S. Plant Patent Application Publication No. 2004/0025211 P1)).

*Overall shape*.—Spreading.

*Height*.—Approximately 3.0 m.

*Width*.—Approximately 1.55 m.

*Caliper*.—Approximately 85 mm on average at 50 mm above the graft union in 4 year old trees on 'M9 T337' rootstock.

*Trunk bark texture*.—Smooth with raised, prominent lenticels.

*Trunk bark color*.—About greyed-green (RHS 197B).

*Patches or other markings*.—No prominent spots or scales are evident.

*Primary branches*.—Stout; branches emerge at an angle of approximately 45 to approximately 60 degrees, with branches higher in the tree emerging at approximately 45 degrees. Measured trees were grown to a central leader system. The typical and observed lateral branch length is 100 cm (first primary branch above the graft union and arising from the main stem).

*Branch color*.—One-year old branches are about light reddish brown in color (RHS 177B), while older branches are about grey-brown in color (RHS 197B).

*Branch pubescence*.—Sparse on the upper half of a one-year-old shoot.

*Branch lenticels*.—Low to medium density, approximately 5 per square centimeter. Shape: Oval. Color: About greyed-white (RHS 156D). Size: Approximately 1.2 mm long by approximately 0.9 mm wide.

*Branch surface texture*.—Smooth.

*Internodes*.—Average internode length is approximately 2.0 cm for a one-year-old shoot.

*Bearing*.—Annual.

*Hardiness*.—European Zone 8 hardy (comparable to 'Royal Gala' (U.S. Plant Pat. No. 4,121) and 'Golden Delicious' (unpatented)).

*Disease and insect resistance*.—Not observed to date.

Leaves:

*Texture*.—Upper surface: Smooth and leathery. Lower surface: Very slightly rugose with some fine pubescence.

*Pubescence*.—Upper surface: Absent to very fine. Lower surface: Fine (light).

*Sheen*.—Glossy.

*Length*.—100 mm.

*Width*.—62 mm.

*Margin*.—Serrate.

*Tip (apex) surface*.—Apiculate.

*Stipules*.—2 present on 90% of leaves. Length: Average 4.0 mm. Width: Average 1.2 mm at base. Upper surface texture: Fine pubescence on the entire surface (i.e. 100% of the surface). Lower surface texture: Fine pubescence on the entire surface (i.e. 100% of the surface). Apex shape: Acicular.

*Leaf color*.—Upper surface: Dark green (RHS 135A). Lower surface: Light yellowish green (RHS 135D).

*Leaf vein color*.—Light green yellowish (RHS 135D).

*Petiole length*.—34 mm.

Flower:

*General*.—Size: Medium. Diameter: Approximately 37.7 mm when fully flattened. Shape: The entire flower is ovoid to round when viewed from above.

*Flower bud*.—Shape: Plump and rounded. Color: Unopened bud: About red-purple (RHS 186B). Opened bud: About white (RHS 155D) with about red-purple (RHS 186C) streaks.

*Petals*.—Number: 5 per flower. Length: 16 mm. Width: 12.5 mm. Shape: Ovate. Base: Acuminate. Apex: Rounded. Arrangement: Separate but overlapping. Color: Upper petal surface: About white (RHS 155D) to about red-purple (RHS 186C). Lower petal surface: About white (RHS 155D) to about red-purple (RHS 186B).

*Sepals*.—Number: About 5 per flower. Shape: Thin deltoid. Apex: Acuminate. Base: Truncated. Length: 7 mm. Width: 3 mm. Color: About green (RHS 143A), tinged at the tip with about red-purple (RHS 59A). Arrangement: Separate.

*Pedicel/peduncle*.—Apples do not have branched inflorescences, and hence do not have pedicels. The flower stalk of an apple is the peduncle. Length: 27.5 mm. Diameter: 1 mm. Color: About yellow-green (RHS 143C).

*Stamen*.—Number: Approximately 20 per flower, arranged in a row around the circumference of the receptacle. Length: 7 mm. Filament color: About white (RHS 155C).

*Anthers*.—Number: About 20 per flower. Color: About yellow (RHS 5D). Unopened anther color: About yellow (RHS 5D). Pollen color: About yellow (RHS 4B).

*Pistil*.—General: Fused styles. Length: 5 mm. Number: Typically 5 pistils per flower. Arrangement in flower: Fused at one third the distance from the basal end, with the fused region being covered in white (RHS 155D) pubescence. Color: Green-yellow (RHS 145B). Color of stigma: About yellow-green (RHS 143C). Color of styles: From the yellow-green group (RHS 145B).

*Pollination requirements*.—An early flowering variety (e.g., 'Braeburn' (unpatented) is preferred). Later flowering varieties (e.g., 'Granny Smith' (unpatented)) will overlap sufficiently in flowering to enable pollination.

*Fragrance*.—Slight, apple-blossom-like.

*Bloom season* (*time of beginning of flowering*).—In 2018 in Sint-Truiden, Belgium, blooming began on the 20$^{th}$ of April, with full bloom on the 23$^{rd}$ of April, and finished on the 26$^{th}$ of April.

Fruit:

*General*.—Measurements are the average of 10 typical 'ZOUK G1' apples. Size: Medium to large. Length: Approximately 65 mm. Width: Approximately 71 mm. Shape: Asymmetrical, conic; slight ribbing is present; very slight lobes are observed at the calyx end. The calyx is slightly open. Basin: Shape: Concave. Width: Approximately 20 mm. Depth: Approximately 4.5 mm. Cavity: Width: Approximately 15 mm. Depth: Approximately 7 mm.

*Fruit stem*.—Length: Approximately 20 mm. Diameter: Approximately 2 mm. Color: About yellow-green (RHS 144B). Locules: 5 slightly open locules with seeds free of the carpel wall at maturity. Length: Approximately 25 mm. Width: Approximately 20 mm.

*Fruit skin*.—Tendency to crack: Very low. Thickness: Medium. Surface texture: Glossy. Lenticels: Present at an average density of about 5 lenticels per square centimeter. Diameter: Approximately 0.5 to 1.0 mm. Color: Generally orange-yellow (RHS 165C). Color: General color effect: Striped about vivid red (RHS 46B). Ground color: At maturity, about brilliant greenish-yellow (RHS 3B). Over color: About vivid red (RHS 46B). Pattern of over color: Solid flush with weak stripes. Width of fruit stripes: Narrow. Russetting: Small area of slight russetting around the stalk attachment and eye basin. Bloom: Moderate.

*Flesh*.—Flavor: Mild, sweet, and low acid. Brix: Approximately 14.1. Juiciness: Moderately juicy. Color: About pale yellow (RHS 8D). Aroma: Apple-like and moderate in intensity (very similar to 'Royal Beaut' (U.S. Plant Patent Application Publication No. 2004/0025211 P1)). Firmness: Medium.

*Core*.—The calyx and calyx tube are closed and the core lines are defined. Shape: Round to slightly elongate. Diameter: Approximately 20 mm. Number of bundles: Approximately 10 per fruit. Core length: Approximately 25 mm. Calyx tube length: Approximately 15 mm (measured as the length from the calyx end at the point of sepal attachment to the point of calyx tube closure).

*Seed*.—Number: About 1 to 2 per cell. Shape: Acute. Length: Approximately 8 mm. Width: Approximately 5 mm. Color: About greyed-orange (RHS 165A).

*Fruit production*.—During the 2018 season in Sint-Truiden, Belgium, the first picking date was about the 20$^{th}$ of August and the last picking date was about the 27$^{th}$ of August. Fruits mature for commercial harvesting approximately in the last week of August in the Haspengouw area in Belgium.

*Time of fruit eating maturity*.—During the 2018 season in Sint-Truiden, Belgium, the time of fruit eating maturity was August 17$^{th}$.

*Usage*.—Fresh eating.

*Storage*.—Fruit remains fresh at room temperature (approximately 20° C.) for approximately 7 days and can be stored up to approximately 10 months in cold storage (about 1° C., or about 34° F.).

*Shipping quality of fruit*.—Good.

*Productivity of fruit*.—About 20 kilograms for a 4 year-old tree.

Comparison to Parental Variety

Apple tree variety 'ZOUK G1' is distinguished from 'Royal Beaut' (U.S. Plant Patent Application Publication No. 2004/0025211 P1) by the following unique combination of characteristics: fruit of 'ZOUK G1' mature in color about one month (4 weeks) earlier than fruit of 'Royal Beaut'; and 'ZOUK G1' produces a higher percentage of fully colored fruit as compared to 'Royal Beaut', which results in higher yield of first class quality fruit plus fewer picking rounds needed at harvest.

Figure 5A:
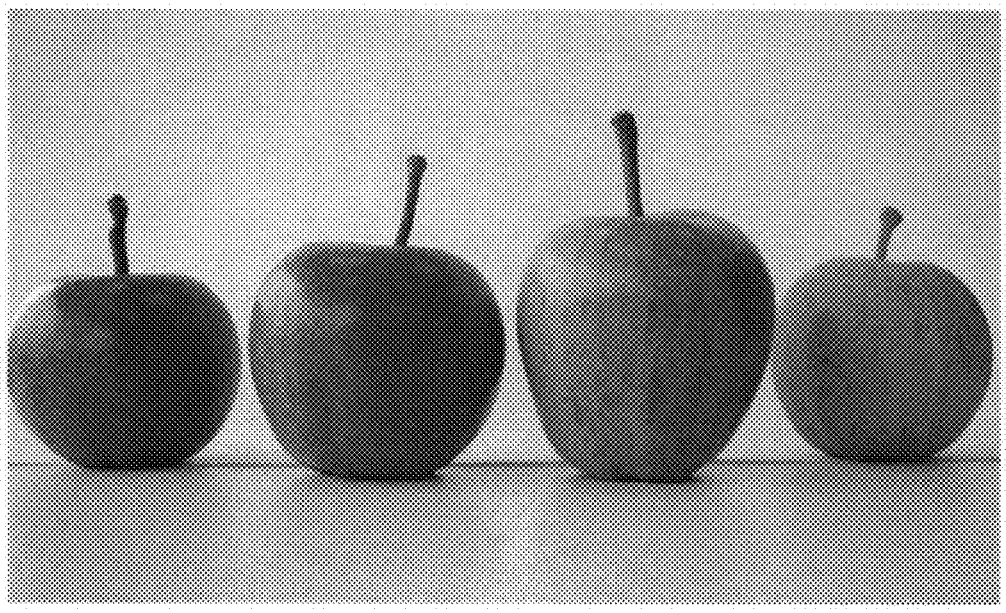
FIGS. 5A-5D illustrate the differences in color during ripening between whole fruit of apple tree variety 'ZOUK G1' and 'Royal Beaut'.
Figure 5B:
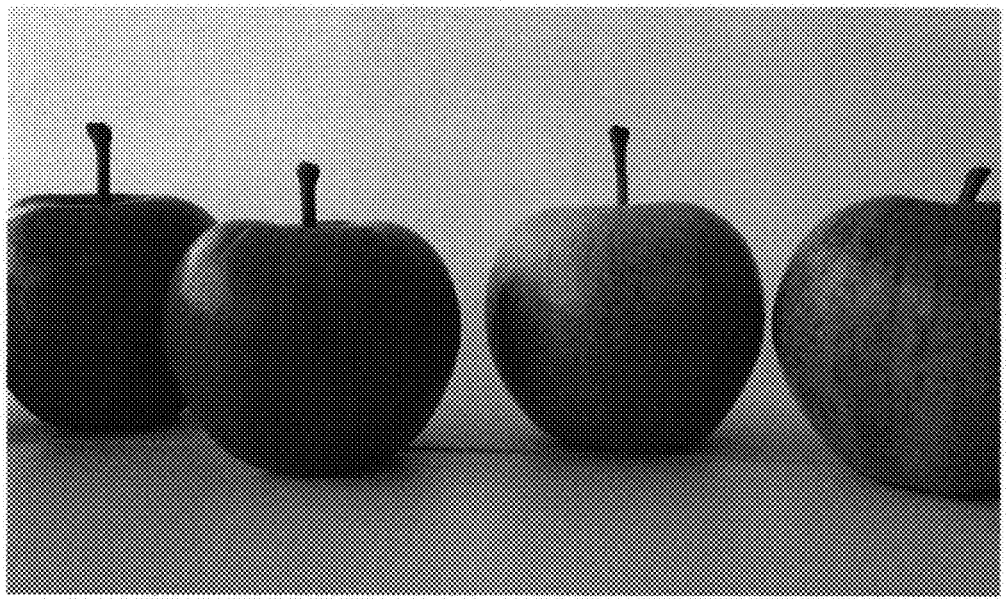
Figure 5C:
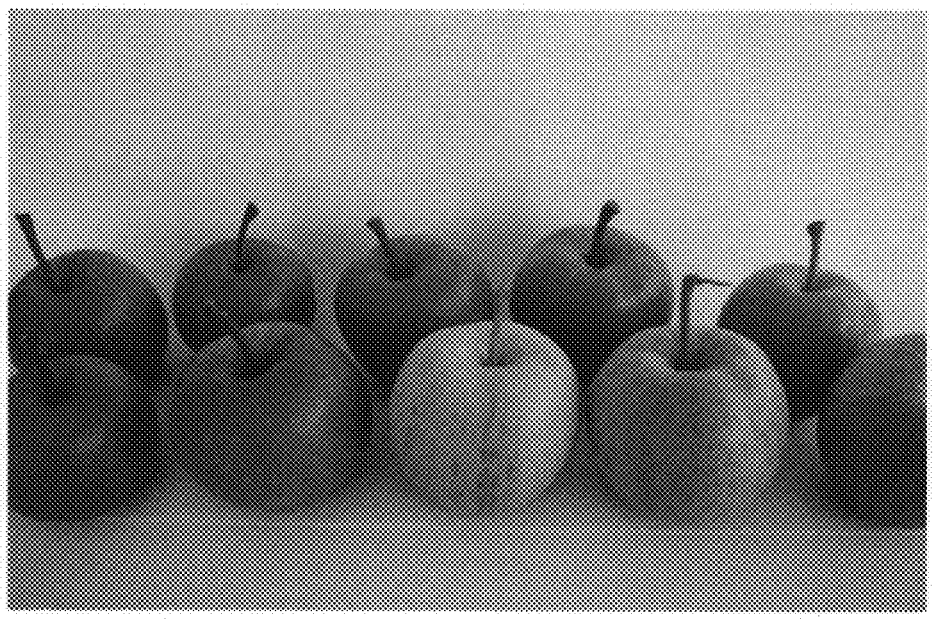
Figure 5D:
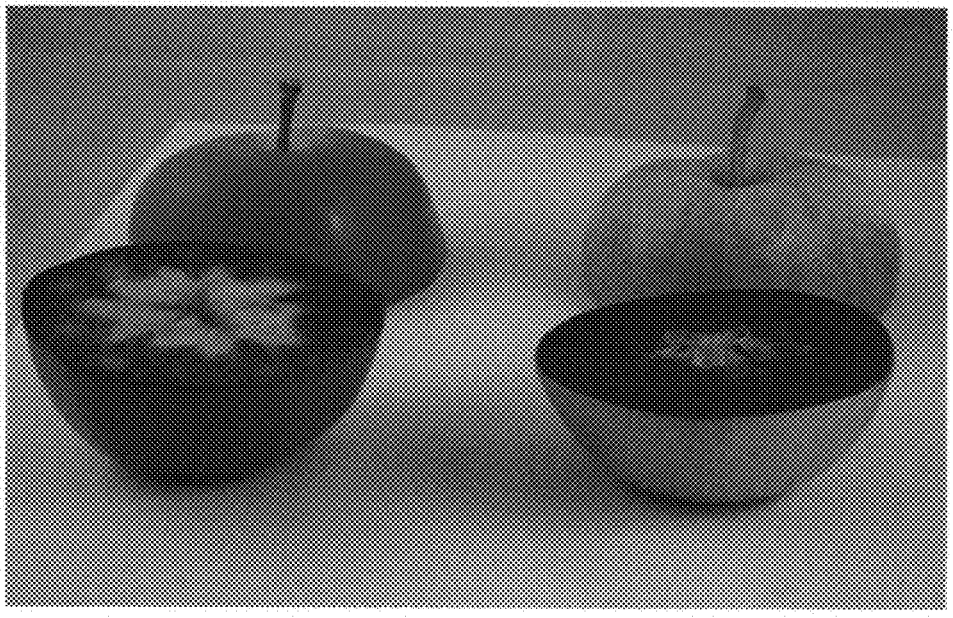

Apple tree variety 'ZOUK G1' is further distinguished from 'Royal Beaut' in that 'ZOUK G1' fruit has a time to maturity (i.e. ripeness) that is 10 days earlier than that of 'Royal Beaut' (August 24 for 'ZOUK G1' as compared to September 4 for 'Royal Beaut'). FIG. 5D shows the results of an iodine staining test, which is a test for starch conversion. Whole fruit of apple tree variety 'ZOUK G1' (on the left) and 'Royal Beaut' (on the right) were cut in half, and an iodine solution was applied to the cut (i.e., interior) surface. The iodine solution stains the surface of the fruit black when starch is present (i.e., has not been converted), while a lack of black staining indicates that starch has been converted into simple sugars. Fruit that are ready to eat are generally about 85% unstained in an iodine staining test. FIG. 5D shows that apples of the 'ZOUK G1' variety exhibit less iodine staining than apples of the 'Royal Beaut' variety of the same age (image taken 3 days before harvest of 'ZOUK G1'), meaning that fruit of 'ZOUK G1' ripen and are ready to eat earlier than fruit of the 'Royal Beaut' variety.

'ZOUK G1' also flowers about one week earlier than does 'Royal Beaut'. 'ZOUK G1' is very high yielding and is less sensitive to frost. Further, 'ZOUK G1' and 'Royal Beaut' fruit picked at maturity during year 4 (Aug. 25, 2017 for 'ZOUK G1' and Sep. 1, 2017 for 'Royal Beaut') had the maturity indices shown in Table 1, below. The pressure of 'ZOUK G1' fruit at time of maturity is slightly elevated as compared to the pressure of 'Royal Beaut' fruit at maturity.

TABLE 1

Characteristics of 'ZOUK 1' and 'Royal Beaut' fruit at maturity. Maturity indices

| Variety | Pressure (Newton) | °Brix |
|---|---|---|
| 'ZOUK G1' | 9 | 13 |
| 'Royal Beaut' | 8 | 13 |

Comparison to Closest Related Known Varieties

TABLE 2

Compares some of the characteristics of the 'ZOUK G1' apple tree variety with the similar apple tree varieties, 'BL-14' (U.S. Plant Pat. No. 27,867), 'Gala Schnico Red' (U.S. Plant Pat. No. 27,577), and 'Zouk 32' (U.S. Plant Pat. Application No. 15/732,497).

| Characteristic | 'Zouk G1' | 'BL-14' |
|---|---|---|
| Branch color | One-year old branches are about light reddish brown in color (RHS 177B), white color branches are about grey-brown in color (RHS 197B) | Grey-brown group 199A (scaffold branches) |
| Hardness | European Zone 6 | USDA Zone 6b |
| Peticle length | 34 mm | 28.5 mm |
| Petal color | Upper partial surface: About white (RHS 155D) to about red-purple (RHS 185C) Lower petal surface: About white (RHS 155D) to about red-purple (RHS 186B) | Background color is white (20%), over color both upper and lower surfaces is variable in the red-purple group 62D and 63A |
| Fruit shape | Asymmtrical, conic | Round conical |
| Fruit skin color at harvest | Striped about vivid red (RHS 46B). Ground color: at maturity, about brilliant greenish-yellow (RHS 3B) Over-color: About vivid red (RHS 46B) | Wash under color from the red group 47A, stripe over color from the red group 46A |
| Brix | 13° | 12.5° |
| Sead shape | Acute | Mostly obtuse with occasional acute |
| Seed color | about greyed-orange (RHS 165A) | From the greyed-orange group 177A |

| Characteristic | 'Gala Schnico Red' | 'Zouk 32' |
|---|---|---|
| Branch color | Greyish brown | Dark greyish yellowish brown (RHS N199C) |
| Hardness | European Zone B | European Zone B |
| Peticle length | 20 mm | 46 mm |
| Petal color | Color (upper and lower surfaces) = white (CPVO/UPOV Nr 19, Note 1) and light pink (upper) (CPVO/UPOV Nr. 19, Note 3); white (under) (CPVO/UPOV Nr. 19, Note 1) | Upper petal surface: White (RHS NN155D) with streaks of pale purplish pink (RHS 62D). Lower petal surface: About white (RHS N155D) to moderate purplish pink (RHS 62B) |
| Fruit shape | Conical | Globose-conical, slightly elongated |
| Fruit skin color at harvest | The hue of over colour with bloom removed is purple red (CPVO/UPOV Nr. 37, Note 4) | General color effect; Vivid reddish orange (RHS 42A). Ground color: At maturity, about brilliant yellow (RHS 14C). Over color: About red (RHS 42A) |
| Brix | 11-12° | Average approximately 15° |
| Sead shape | Elliptic | Acute |
| Seed color | Red brown | Moderate brown (RHS 165A) |

What is claimed is:

1. A new and distinct variety of apple tree named 'ZOUK G1' as shown and described herein.

* * * * *